US006874909B2

(12) United States Patent
Vanderschuit

(10) Patent No.: US 6,874,909 B2
(45) Date of Patent: Apr. 5, 2005

(54) MOOD-ENHANCING ILLUMINATION APPARATUS

(76) Inventor: Carl R. Vanderschuit, 751 Turquoise St., San Diego, CA (US) 92109

(*) Notice: Subject to any disclaimer, the term of this patent is extended or adjusted under 35 U.S.C. 154(b) by 0 days.

(21) Appl. No.: 10/341,239

(22) Filed: Jan. 13, 2003

(65) Prior Publication Data

US 2004/0136189 A1 Jul. 15, 2004

(51) Int. Cl.[7] .................... F21S 2/00

(52) U.S. Cl. .................... 362/232; 362/284; 362/806; 362/812

(58) Field of Search .................... 362/35, 232, 235, 362/240, 245, 246, 282, 284, 328, 348, 363, 806, 811, 812, 104

(56) References Cited

U.S. PATENT DOCUMENTS

| | | | | |
|---|---|---|---|---|
| 1,081,800 A | * 12/1913 | Wiley et al. | ................ | 362/812 |
| 1,747,556 A | * 2/1930 | Price | ................ | 362/232 |
| 1,771,710 A | * 7/1930 | Gover | ................ | 362/806 |
| 1,830,026 A | * 11/1931 | Harase | ................ | 362/812 |
| 1,833,498 A | * 11/1931 | Prouty | ................ | 362/812 |
| 3,791,058 A | * 2/1974 | Mollica | ................ | 362/806 |
| 3,793,755 A | * 2/1974 | Gersch et al. | ................ | 362/811 |
| 5,555,658 A | 9/1996 | Yu | | |

FOREIGN PATENT DOCUMENTS

| | | |
|---|---|---|
| CH | 662 931 A | 11/1987 |
| DE | 299 18 185 U | 1/2000 |
| EP | 0 231 471 A | 8/1987 |
| GB | 2 392 973 A | 3/2004 |
| WO | WO 93 18358 A | 9/1993 |

OTHER PUBLICATIONS

U.S. Appl. No. 10/189,822, filed Jul. 3, 2002, Vanderschuit, pending, entitled Beverage Accessory Device.

U.S. Appl. No. 10/606,314, filed Jun. 25, 2003, Vanderschuit, pending, entitled Lighted Hat.

U.S. Appl. No. 10/606,324, filed Jun. 25, 2003, Vanderschuit, pending, entitled Lighting Device.

U.S. Appl. No. 10/606,325, filed Jun. 25, 2003, Vanderschuit, pending, entitled Lighted Hat.

U.S. Appl. No. 10/786,995, filed Feb. 25, 2004, Vanderschuit, pending, entitled Therapeutic Device And Methods For Applying Therapy.

Supplemental European Search Report dated May 13, 2004; App. No. EP 01 939 305.7;6 pages.

U.S. Appl. No. 10/797,251, filed Mar. 10, 2004, Vanderschuit, pending, entitled Lighted Balloons.

U.S. Appl. No. 10/851,510, filed May 21, 2004, Vanderschuit, pending, entitled Illuminated Implements For Drinking And/Or Eating And Related Methods.

United Kingdom Combined Search and Examination Report dated Jan. 6, 2004; Application No. GB 0326549.3;4 pages.

Supplementary European Search Report dated Mar. 1, 2004; App. No. EP 01 93 9305;3 pages.

* cited by examiner

*Primary Examiner*—Y. My Quach-Lee
(74) *Attorney, Agent, or Firm*—Harness, Dickey & Pierce, P.L.C.

(57) ABSTRACT

An illumination apparatus that includes a housing, at least one light source and a light-altering device. The light-altering device is positioned relative to the housing and the light source for receiving and altering light from the light source such that the altered light illuminates at least one of a portion of the housing and a portion of a surface supporting the illumination apparatus.

23 Claims, 4 Drawing Sheets

110
128
120
112
128
128
147
118
115
129
116
116
114
114
136
114
114
114

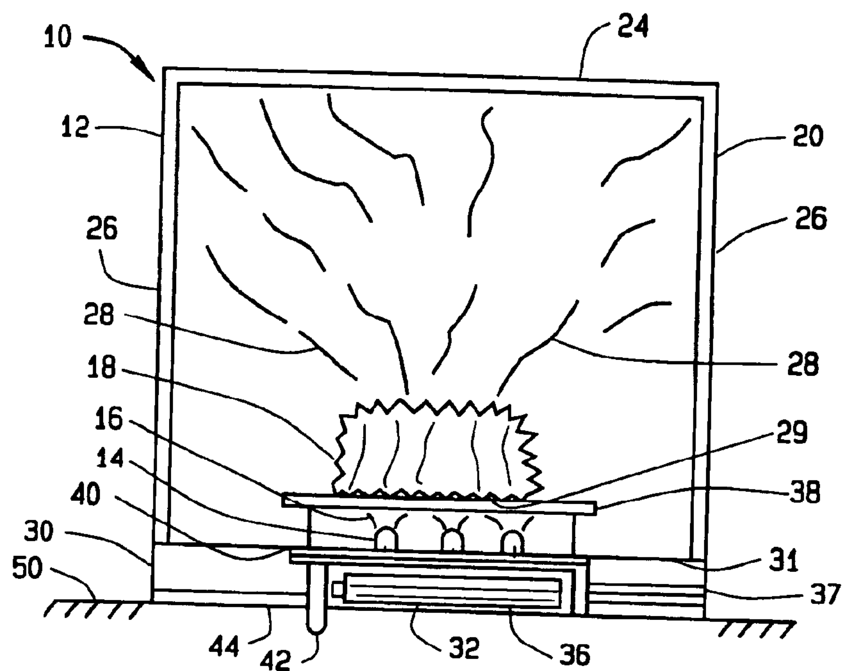
FIG. 1
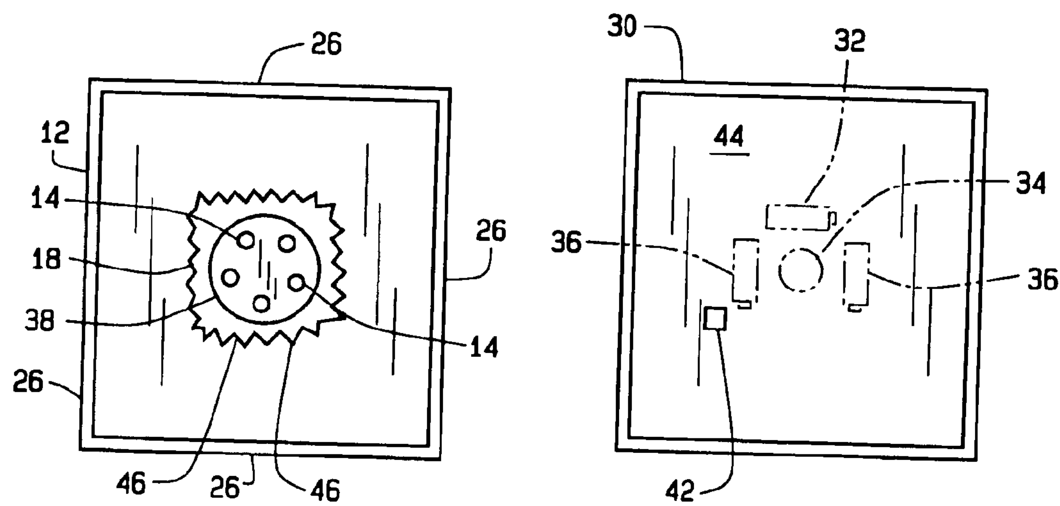
FIG. 2
FIG. 3

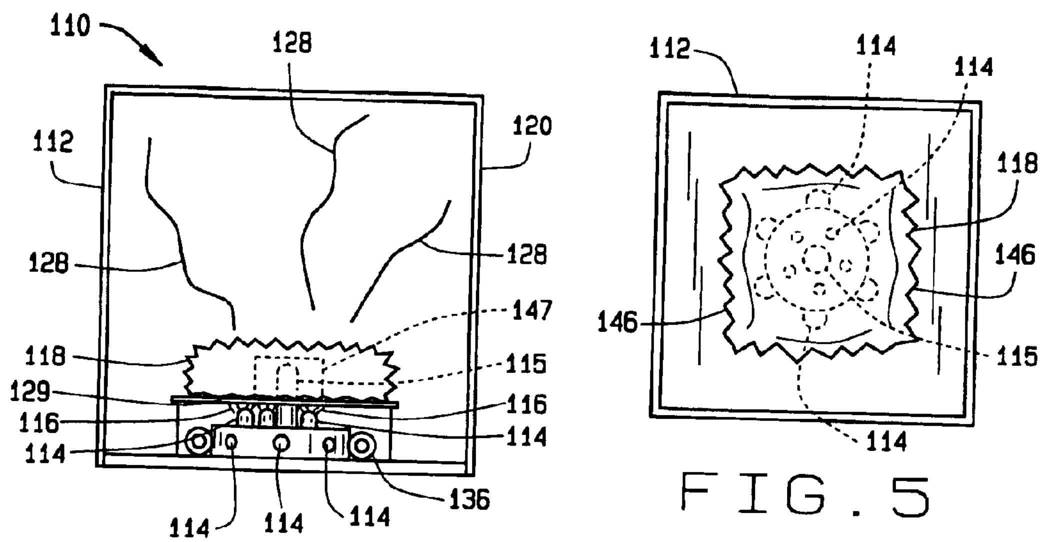
FIG. 4
FIG. 5
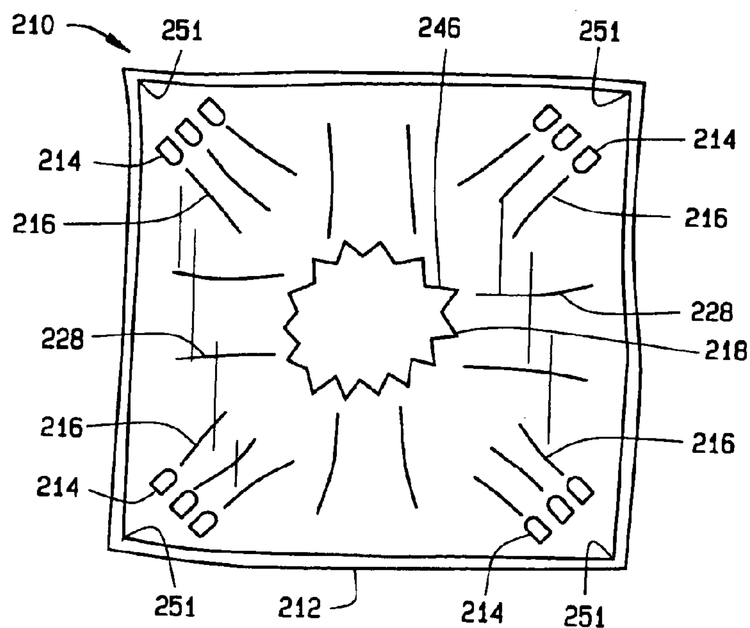
FIG. 6

MOOD-ENHANCING ILLUMINATION APPARATUS

FIELD OF THE INVENTION

The present invention relates generally to light sources and more particularly to illumination apparatus that provide mood lighting or atmospheric-enhancing illumination, such as visually pleasing light effects and patterns.

BACKGROUND OF THE INVENTION

Illumination devices, such as lava lamps, have been used for many years to provide atmospheric-enhancing illumination or mood lighting. Even today, there still exists a continuing demand and need for illumination devices that provide visually-pleasing illumination effects and light patterns.

In addition, jewelry, hair ornaments, and other accessory items are being provided with light sources, such as light-emitting diodes, that draw attention to the accessory item and its user. However, the inventor has recognized that these light sources are typically positioned to emit light outwardly from the accessory item without illuminating the accessory item itself, which would provide a more stimulating and pleasing visual effect.

SUMMARY OF THE INVENTION

In order to solve these and other needs in the art, the inventor hereof has succeeded in designing an illumination apparatus that in one exemplary embodiment includes a housing, at least one light source and a light-altering device. The light-altering device is positioned relative to the housing and the light source for receiving and altering light from the light source such that the altered light illuminates at least one of a portion of the housing and a portion of a surface supporting the illumination apparatus.

Further areas of applicability of the present invention will become apparent from the detailed description provided hereinafter. It should be understood that the detailed description and specific examples below, while indicating exemplary embodiments of the invention, are intended for purposes of illustration only and are not intended to limit the scope of the invention.

BRIEF DESCRIPTION OF THE DRAWINGS

The present invention will be more fully understood from the detailed description and the accompanying drawings, wherein:

FIG. 1 is a side view of an illumination apparatus according to one embodiment of the present invention;

FIG. 2 is a top view of the illumination apparatus shown in FIG. 1;

FIG. 3 is a bottom view of the illumination apparatus shown in FIG. 1;

FIG. 4 is a side view of an illumination apparatus according to another embodiment of the present invention;

FIG. 5 is a top view of the illumination apparatus shown in FIG. 4;

FIG. 6 is a top view of an illumination apparatus configured to illuminate a support surface according to another embodiment of the present invention;

Corresponding reference characters indicate corresponding features throughout the drawings.

DETAILED DESCRIPTION OF EXEMPLARY EMBODIMENTS

Figure 7:
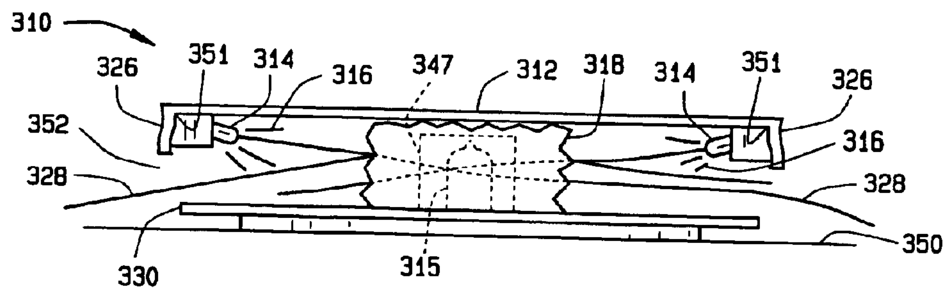
FIG. 7 is a side view of an illumination apparatus configured to illuminate a support surface according to another embodiment of the present invention.

Referring to FIG. 1, there is shown an illumination apparatus, generally indicated by reference number 10, according to one embodiment of the present invention. As shown in FIG. 1, the illumination apparatus 10 includes a housing 12, at least one light source 14, and a light-altering device 18. The light-altering device 18 is positioned relative to the housing 12 and the light source 14 for receiving and altering light 16 from the light source 14 such that the altered light 28 illuminates at least a portion of the housing 12, such as the upper portion 20 of the housing 12. Alternatively, or additionally, the light-altering device 18 may be positioned relative to the housing 12 and the light source 14 such that the altered light 28 illuminates at least a portion of a surface 50 supporting the illumination apparatus 10, such as a wall, ceiling, floor, tabletop, walkway, clothing, a surface of a mobile platform, etc. During operation, the light-altering device 18 refracts, reflects, diffracts, and/or disperses the light 16 such that the altered light 28 illuminates the portion (s) of the housing 12 and/or the support surface 50 with mood-enhancing light patterns and effects.

Figure 9:
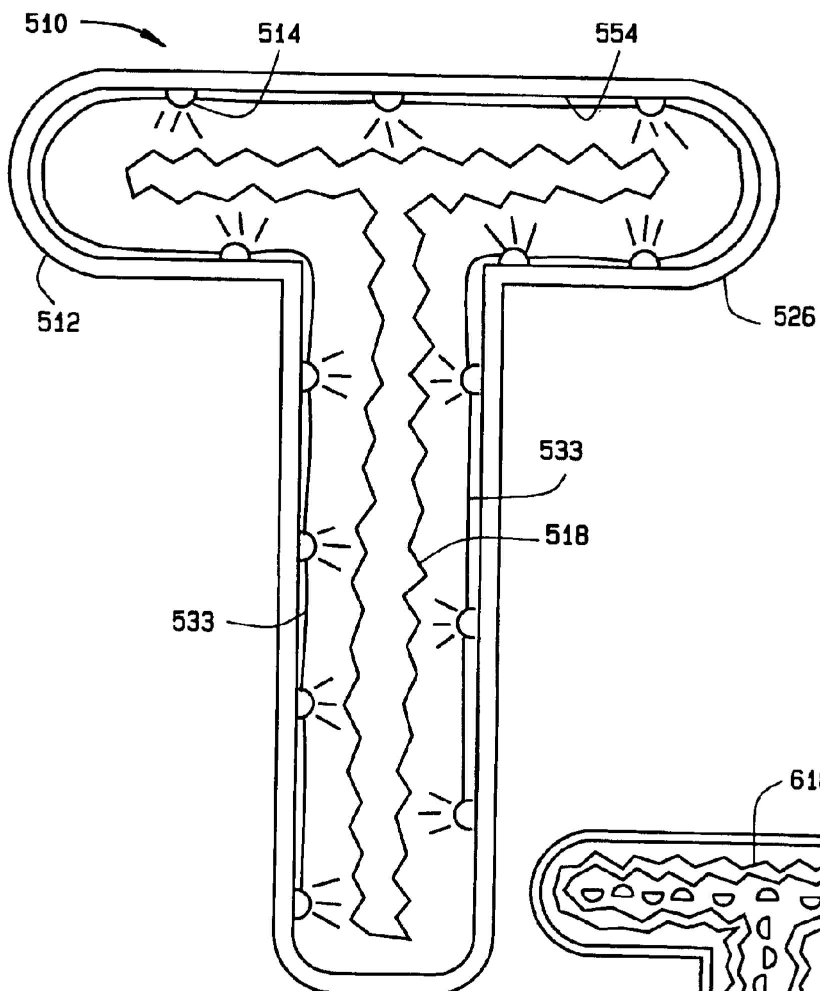
FIG. 9 is a top view of an illumination apparatus configured in a shape of a letter "T" according to another embodiment of the present invention.
Figure 10:
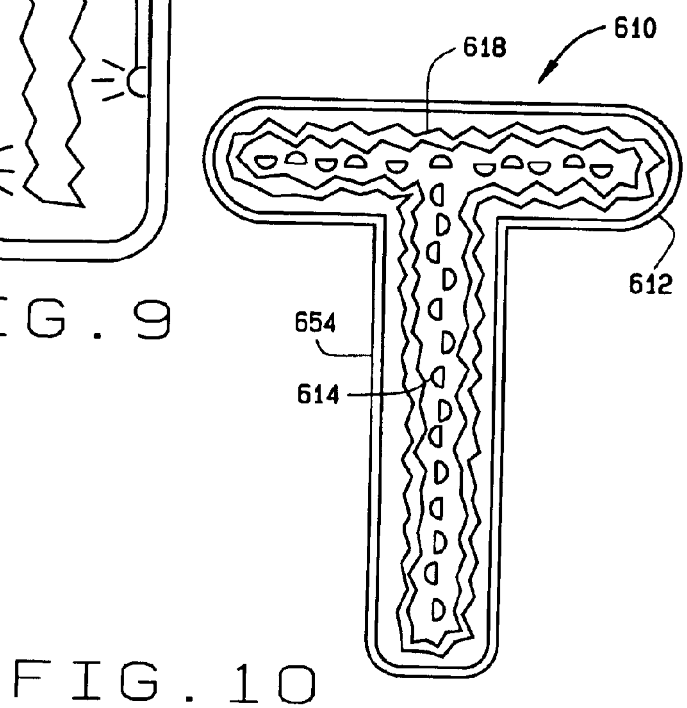
FIG. 10 is a top view of an illumination apparatus configured in a shape of a letter "T" according to another embodiment of the present invention.

In the exemplary embodiment shown in FIGS. 1 through 3, the housing 12 is substantially cube-shaped and decorated to resemble an ice cube or ice berg. It is to be understood, however, that the housing 12 may comprise any of a wide range of other shapes including, but not limited to, fruits, tear drops, rain drops, alphanumeric characters, pyramids, etc. By way of example, and as explained in greater detail below, FIGS. 9 and 10 illustrate apparatus 510 and 610 shaped as the letter "T".

A wide range of materials may be used for the housing 12 including, but not limited to, acrylics, glasses, plastics, among others. The surfaces of the housing 12 may be transparent, translucent, opaque, reflective, or a combination thereof. In the exemplary embodiment shown in FIGS. 1 through 3, the housing surface 24 positioned opposite the support surface 50 is transparent, whereas the housing side surfaces 26 are translucent or frosted to diffuse or soften the altered light 28.

To allow ready access to the light source 14, the light-altering device 18 and/or the interior of the housing 12, the illumination apparatus 10 further includes a readily removable base assembly 30. The base assembly 30 may be attached to the housing 12 using a suitable fastening system or method (e.g., an interference fit, adhesives, threaded members, resilient ribs, among others). By way of example only, the housing 12 includes an open end 31 sized to be received over and supported by the base assembly 30. Several inwardly extending resilient knobs or protuberances (not shown) are positioned on the housing side surfaces 26 adjacent the open end 31. When the housing 12 is fitted over the base assembly 30, the knobs engage the base assembly 30 to create an interference or friction fit between the housing 12 and the base assembly 30. Alternatively, the base assembly 30 and housing 12 can be formed as a single unit.

Depending on the particular application in which the illumination apparatus 10 is to be used, the illumination apparatus 10 may be configured for placement upon a horizontal support surface, such as a tabletop or desktop. Alternatively, the illumination apparatus 10 can be configured to be mounted on a wall, retrofitted to (e.g., mounted and electrically connected to) an existing wall or ceiling junction box, or attached to a surface of a mobile platform, such as an automobile.

The base assembly 30 further includes a power source 32 switchably connected to the light source 14. In the illustrated embodiment, the power source 32 comprises batteries 36 and an AC adapter port 37 to allow the illumination apparatus 10 to receive power through an electrical cord connected with a standard wall outlet. It should be noted, however, that the power source 32 contemplates any suitable means of providing energy to the light source 14 including, but not limited to, renewable batteries, rechargeable batteries, disposable batteries, and other suitable power sources that may be either external or internal to the illumination apparatus 10. If rechargeable, the power source may be rechargeable by solar, magnetic, electrical, and chemical means, and the like or any combination thereof. Accordingly, the power source mechanism should not be limited to the power source mechanisms described and shown herein.

In the exemplary embodiment of FIG. 1, the base assembly 30 also includes an actuator system for rotating the light-altering device 18 with respect to the light source 14. The actuator system includes a turntable 38 having a transparent support surface for supporting the light-altering device 18. The turntable 38 is coupled to a motor 34 that when energized rotates the turntable 38 and the light-altering device 18 thereon. Alternatively, the actuator system could instead be used to rotate the light source 14 relative to the light-altering device 18.

The light source 14 in the exemplary embodiment 10 comprises a plurality of variously colored light-emitting diodes positioned adjacent an end portion 29 of the light-altering device 18. Alternatively, any suitable light source may be employed including but not limited to fiber optics, halogen, incandescent, laser, fluorescent, magnetic, and the like.

The operation of the light source 14 and the actuator system (i.e., motor 34 and turntable 38) are controlled by a controller in accordance with user input. In one embodiment, the controller includes an integrated circuit/circuit board assembly 40 (i.e., a integrated circuit board mounted on a circuit board) and a switch 42. The switch 42, for example, may allow the user to select from a plurality of predetermined rotational speeds for the turntable 38. Or for example, the switch 42 may allow the user to select from among various display modes for the light source 14. Such display modes may include an off mode, a mode during which the light-emitting diodes blink in a predetermined sequence, and a mode during which the light-emitting diodes pulsate to sounds. The sounds may be produced by the apparatus 10 itself (e.g., via a speaker built-in to the apparatus 10) or a source external to the apparatus 10 (e.g., ambient sounds).

In the illustrated embodiment, the switch 42 comprises a push button switch disposed on a bottom portion 44 of the base assembly 30. However, and depending on the application in which the illumination apparatus 10 will be used, the switch 42 may comprise any one of a wide range of other suitable switch means. For example, the switch 42 may be provided on a cord extending from the base assembly 30. Or for example, the controller may be configured for use with an infrared remote control. In a further embodiment, the switch 42 may be disposed adjacent a lower portion of a flexible surface of the housing 12 such that application of pressure to the flexible surface causes the switch 42 to change setting.

The light-altering device 18 will now be described in more detail. As shown in FIG. 1, the light-altering device 18 is positioned on the turntable 38, which, in turn, is positioned above the light-emitting diodes 14. The light-altering device 18 and the light-emitting diodes 14 are positioned within the housing 12 at a substantially central location relative to the housing 12. The light-altering device 18 alters the light 16 from the light source 14 such that the upper portion 20 of the housing 12 is illuminated with the altered light 28. The altered light 28 is directed upwards through the transparent housing surface 24 and outwards through the translucent housing side surfaces 26, thus providing the room in which the illumination apparatus 10 is being used with mood-enhancing light patterns and effects. Alternatively, the light-altering device and the housing may be integrally formed as a single component. For example, the light-altering device may comprise an internal faceted surface of the housing.

The light-altering device 18 in the exemplary embodiment of FIGS. 1 through 3 comprises facets 46. Although not limited to any particular material, the light-altering device 18 may comprise a transparent material such as polished acrylic material, glass, plastic, crystal, among others. Alternatively, the light-altering device 18 may comprise a translucent or reflective material.

The light-altering device 18 can have a variety of shapes. In the illustrated embodiment, the light-altering device 18 is shaped in a substantially similar manner as the housing 12 (e.g., cube-shaped as in FIGS. 1 and 2, shaped as the letter "T" in FIG. 9). In other embodiments, the light-altering device may be substantially spherical, pyramidal, prismatic, among other shapes depending on the application for which the illumination apparatus 10 will be used.

The illumination apparatus 10 may further include one or more indicia positioned to receive the light 16 from the light source 14 and/or to receive the altered light 28 from the light-altering device 18. The indicia may be at least partially opaque, translucent, or a combination thereof such that the light 16 and/or the altered light 28 produces a silhouette of the indicia that is displayed to a user. The indicia may include any of a wide range of symbols, characters, shapes, words, logos, combinations thereof, etc.

Depending on the particular placement of the indicia, the illumination apparatus 10 may display the silhouette within the housing 12 and/or on a surface external to the housing 12, such as the support surface 50. In exemplary embodiments, the indicia is disposed on an interior surface of the housing 12, suspended within the hollow interior of the housing 12, and/or disposed on an external surface of the light-altering device 18.

Referring to FIGS. 4 and 5, there is shown an illumination apparatus 110 according to another exemplary embodiment of the present invention. The illumination apparatus 110 includes a housing 112, at least one light source 114 for emitting light 116, and a light-altering device 118 positioned to receive the light 116 from the light source 114. The light-altering device 118 is positioned relative to the housing 112 and the light source 114 for receiving and altering the light 116 from the light source 114 such that the altered light 128 illuminates at least an upper portion 120 of the housing 112. The light-altering device 118 refracts, reflects, diffracts, and/or disperses the light 116 such that the altered light 128 illuminates the upper housing portion 120 with mood-enhancing light patterns and effects.

As shown in FIGS. 4 and 5, the illumination apparatus 110 also includes at least one other light source 115 for providing ambient lighting (such as for reading) much like a conventional lamp or light fixture. The illumination apparatus 110 may be configured such that the light sources 114 and 115 operate independent from one another. Accordingly, a user may turn on or off either one or both the light sources 114 and 115, depending on the illumination effect desired.

In the illustrated embodiment, the light source 114 comprises a plurality of light-emitting diodes positioned adjacent the end portion 129 of the light-altering device 118, which includes a plurality of facets 146. The light-altering device 118 is disposed at a centrally located position within the housing 112. The light source 115 comprises an incandescent light disposed at least partially within a hollow interior or cavity 147 defined by the light-altering device 118.

FIGS. 6 and 7 illustrate exemplary embodiments of an illumination apparatus 210, 310 configured to illuminate at least a portion of the surface supporting the apparatus 210, 310. The light-altering device 218, 318 is disposed at a substantially central location relative to the housing 212, 312 and the light source 214, 314 comprises at least one light-emitting diode positioned in each corner 251, 351 of the housing 212, 312. Each light-emitting diode is oriented to emit light towards the light-altering device 218, 318 and the surface 350 supporting the apparatus 210, 310. During operation, the light-altering device 218 refracts, reflects, diffracts, and/or disperses the light 216, 316 such that the altered light 228, 328 illuminates the surface 350 supporting the apparatus 210, 310 with mood-enhancing light patterns and effects.

In the exemplary embodiment shown in FIG. 7, the housing side surfaces 326 are truncated such that a gap 352 is defined between the housing 312 and the mounting plate 330. Accordingly, the altered light 328 passes through the gap 352 and then illuminates the support surface 350. It should be noted that although the apparatus 310 is shown supported by a floor or tabletop, the apparatus 310 can also be mounted to a wall or ceiling.

With further reference to FIG. 7, the illumination apparatus 310 further includes an optional light source 315 for providing normal lighting conditions. In the illustrated embodiment, the light source 315 comprises an incandescent light disposed at least partially within a hollow interior or cavity 347 defined by the light-altering device 318, with the light-altering device 318 disposed substantially around the optional light source 315.

Figure 8:
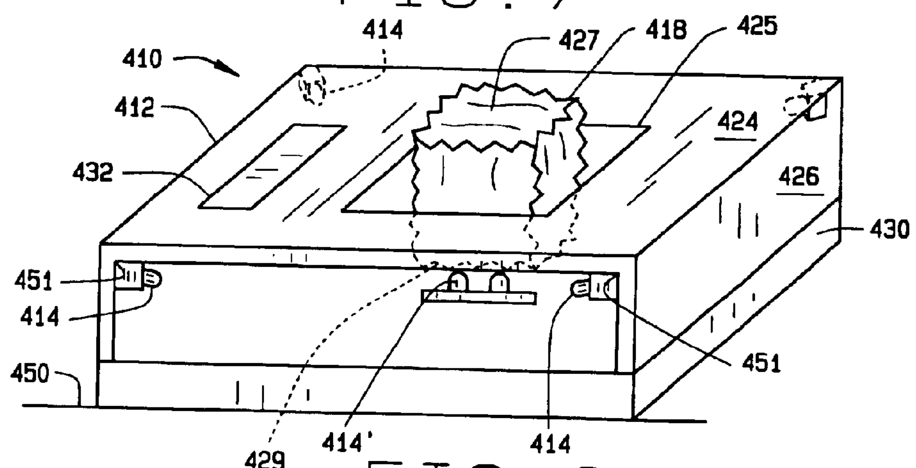
FIG. 8 is a perspective view of an illumination apparatus configured to illuminate a support surface and to illuminate a housing portion positioned opposite the support surface according to another embodiment of the present invention.

In FIG. 8, there is shown an illumination apparatus 410 configured to illuminate at least the surface 450 supporting the apparatus 410 in accordance with another embodiment of the present invention. As shown, the light-altering device 418 is disposed at a substantially central location within the housing 412, and the light source 414 comprises at least one light-emitting diode positioned in each corner 451 of the housing 412. Each light-emitting diode 414 is oriented to emit light towards the light-altering device 418 and the support surface 450. During operation, the altered light travels outward from the light-altering device 418 and toward the surface 450. The altered light then passes through the substantially transparent housing side surfaces 426 to illuminate the support surface 450 with a pleasing light pattern or effect.

To further enhance the illumination effect provided by the apparatus 410, the housing surface 424 opposed the support surface 450 is opaque. The housing surface 424 also defines an opening 425 through which an end portion 427 of the light-altering device 418 extends. In addition, the light source 414 may further include optional light-emitting diodes 414' positioned adjacent the other end portion 429 of the light-altering device 418.

As before with the apparatus 10 shown in FIG. 1, the illumination apparatus 410 in the illustrated embodiment includes a base assembly 430 removably attached to the housing 412. The base assembly 430 may further include the optional light-emitting diodes 414', an actuator system for rotating the light-altering device 418 relative to the optional light-emitting diodes 414', and a power source 432 (e.g., batteries, etc.) switchably connected to the light-emitting diodes 414, 414' and the actuator system. In the illustrated embodiment, the power source 432 includes a solar cell disposed on the housing surface 424, although other suitable means of providing energy to the light sources and the actuator system may be employed.

The operation of the light-emitting diodes 414, 414' and the actuator system may be controlled by a controller in accordance with user input similar to the manner described for the first embodiment 10. For example, the controller may allow the user to choose to have the various light-emitting diodes 414 and 414' blink, activate/deactivate at different times, or to pulsate in accordance with sound from a source external and/or internal to the apparatus 410.

Referring now to FIGS. 9 and 10, there are shown exemplary embodiments of the illumination apparatus 510 an 610, respectively, that are configured for use as signage. In the illustrated embodiments, the apparatus 510 and 610 are formed in the shape of the letter "T". In other embodiments, the housing may be shaped as words, numbers, messages, signs, etc.

As shown in FIG. 9, the light source 514 includes a plurality of light-emitting diodes electrically connected to one another by a way of a electrically-conducting wire 533 or other suitable electrical conductor. The light-emitting diodes are spaced along the perimeter 554 of the housing 512 as defined by the sides 526 of the housing 512. The sides 526 of the housing 512 may be either opaque, translucent, transparent, reflective, or a combination thereof. The surface positioned opposite the surface supporting the apparatus 510 may be either transparent, translucent, or a combination thereof. In addition, the light-altering device 518 is centrally located within the housing 512 and is shaped in a manner similar to that of the housing perimeter 554, which in the illustrated embodiment is the letter "T". Alternatively, one or more light-altering devices may instead be positioned on or be integrally formed with a housing surface that is either positioned opposite or attached to the support surface. In such an alternative embodiment, the light source is oriented for directing light into the light-altering device.

In the exemplary embodiment shown in FIG. 10, the light-altering device 618 is disposed along the perimeter 654 of the housing 612. The light-emitting diodes 614 are disposed at a substantially central location of the housing 612, with the light-altering device 618 disposed substantially around the light-emitting diodes 614.

Figure 11:
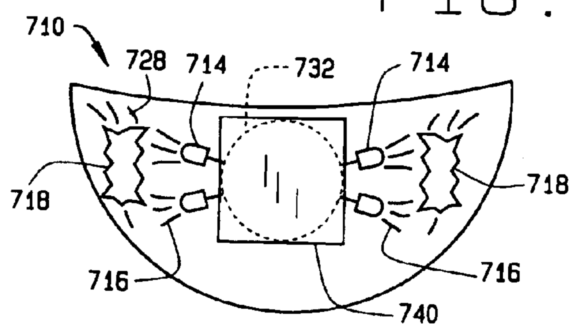
FIG. 11 is a top view of an illuminatable accessory device according to another embodiment of the present invention.
Figure 12:
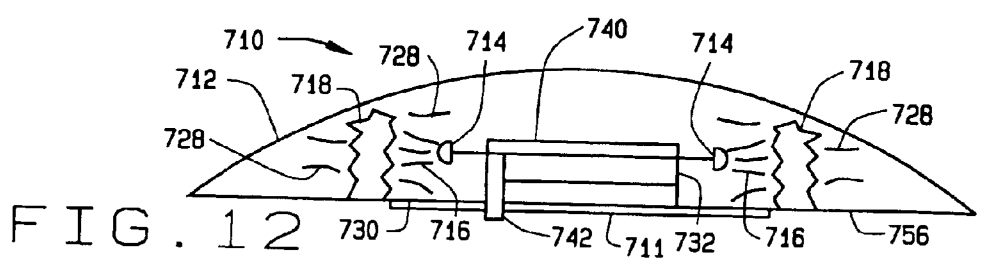
FIG. 12 is a side view of the illumination apparatus shown in FIG. 11.

Referring to FIGS. 11 and 12, there is shown an illumination apparatus 710 configured for use as an illuminating and portable accessory item. In the illustrated embodiment, the illumination apparatus 710 includes an attachment device (e.g., adhesive 711, clip, etc.) for attaching the illumination apparatus 710 to a user, thus allowing the illumination apparatus 710 to be used, for example, as a jewelry, a hair ornament, an illuminating sticker, among other accessory items. Alternatively, the illumination apparatus 710 may also be attached to an automobile hood or other mobile platform surface, for example, to illuminate an automobile emblem or logo.

The illumination apparatus 710 includes a plurality of light-emitting diodes 714 and a light-altering device 718. The light-altering device 718 is positioned relative to the housing 712 and the light-emitting diodes 714 for receiving and altering the light 716 from the light-emitting diodes 714 such that the altered light 728 illuminates at least a portion of the housing 712. Thus, illuminating the accessory item. During operation, the light-altering device 718 refracts, reflects, diffracts, and/or disperses the light 716 (e.g., direction of travel, wavelength, color, phase, etc.) such that the altered light 728 illuminates the portion of the housing 712 with mood-enhancing light patterns and effects. Alternatively, the light-altering device and the housing may be integrally formed as a single component, with the light-altering device comprising an internal faceted surface of the housing.

In the illustrated embodiment, the power source 732 comprises a watch battery. In addition, a rear surface 756 of the base assembly 730 is provided with a suitable adhesive 711 that allows the illumination apparatus 710 to be used as a sticker. The illumination apparatus 710 further includes a controller, such as an integrated circuit/circuit board assembly 740 and a switch 742. The switch 742 allows the user to select from among a plurality of operating modes for the illumination apparatus 710. Alternatively, the controller may include a touch-sensitive switch that when touched by a user activates the illumination apparatus. It should be understood that the other embodiments of the illumination apparatus 10, 110, 210, 310, 410, 510, 610 may also be configured for use as a portable accessory item.

The description of the invention is merely exemplary in nature and is in no way intended to limit the invention, its application, or uses. Thus, variations that do not depart from the substance of the invention are intended to be within the scope of the invention. Such variations are not to be regarded as a departure from the spirit and scope of the invention.

What is claimed:

1. An illumination apparatus, comprising:

a housing;

at least one light source for emitting light;

a light-altering device positioned relative to the housing and the light source for receiving and altering light from the light source such that the altered light illuminates at least one of a portion of the housing and a portion of a surface supporting the illumination apparatus;

a rear surface of the housing;

a user attachment device to allow the housing of the illumination apparatus to be attached to a user, the user attachment device comprising an adhesive disposed on the rear surface of the housing.

2. The illumination apparatus of claim 1, wherein the light-altering device includes a surface having a plurality of facets.

3. The illumination apparatus of claim 2, wherein the light-altering device comprises a substantially transparent material.

4. The illumination apparatus of claim 1, wherein the light-altering device alters the light by at least one of refracting, reflecting, diffracting, and dispersing.

5. The illumination apparatus of claim 1, wherein the housing comprises at least one translucent surface.

6. The illumination apparatus of claim 1, wherein the light source comprises a plurality of light-emitting diodes.

7. The illumination apparatus of claim 1, wherein the illumination apparatus comprises a controller for controlling the operation of the light source in accordance with user input.

8. The illumination apparatus of claim 1, wherein the illumination apparatus is configured for use as a portable, illuminatable accessory item.

9. The illumination apparatus of claim 1, further comprising a base assembly coupled to the housing, the base assembly defining the rear surface on which the adhesive is disposed.

10. An illumination apparatus, comprising:

a substantially cube-shaped housing;

a light-altering device including an end portion;

a plurality of light sources, at least one of which comprises an incandescent or fluorescent light source positioned at least partially within a cavity defined by the light-altering device;

at least one light-emitting diode positioned adjacent the end portion and oriented for directing light into the light-altering device; and the light-altering device being positioned relative to the housing and the light-emitting diode for receiving and altering the light from the light-emitting diode such that the altered light illuminates at least a portion of the housing positioned opposite a surface supporting the illumination apparatus.

11. The illumination apparatus of claim 10, wherein the light-altering device includes a surface having a plurality of facets.

12. The illumination apparatus of claim 10, wherein the light-altering device alters the light by at least one of retracting, reflecting, diffracting, and dispersing.

13. The illumination apparatus of claim 10, further comprising a motor for rotating one of the light-altering device and the light source relative to one another.

14. An illumination apparatus, comprising:

a housing including a side surface;

a light-altering device;

at least one light-emitting diode positioned adjacent a side surface of the housing and oriented for directing light at the light-altering device;

at least one light-emitting diode positioned adjacent each upper corner of the housing and oriented for directing light at the light-altering device, and the light-altering device being positioned at a substantially central location relative to the housing for receiving and altering the light from the light-emitting diodes such that the altered light illuminates at least a portion of a surface supporting the illumination apparatus.

15. The illumination apparatus of claim 14, wherein the light-altering device includes a surface having a plurality of facets.

16. The illumination apparatus of claim 14, wherein the light-altering device alters the light by at least one of refracting, reflecting, diffracting, and dispersing.

17. The illumination apparatus of claim 14, further comprising a motor for rotating one of the light-altering device and the light source relative to one another.

18. An illumination apparatus, comprising:

a housing including a side surface;

a light-altering device;

a plurality of light sources, at least one of which comprises an incandescent or fluorescent light source positioned at least partially within a cavity defined by the light-altering device;

at least one light-emitting diode positioned adjacent a side surface of the housing and oriented for directing light at the light-altering device; and the light-altering device being positioned relative to the housing and the light-emitting diode for receiving and altering the light from the light-emitting diode such that the altered light illuminates at least a portion of a surface supporting the illumination apparatus.

19. An illumination apparatus, comprising:

a housing including a side surface;

a light-altering device;

at least one light-emitting diode positioned adjacent a side surface of the housing and oriented for directing light at the light-altering device;

the light-altering device being positioned relative to the housing and the light-emitting diode for receiving and altering the light from the light-emitting diode such that the altered light illuminates at least a portion of a surface supporting the illumination apparatus;

wherein the housing defines an opening, and wherein the light-altering device is positioned within the housing such that an end portion of the light-altering device extends outwardly through the opening.

20. An illumination apparatus, comprising:

a housing;

at least one light source for emitting light;

a light-altering device positioned relative to the housing and the light source for receiving and altering light from the light source such that the altered light illuminates at least a portion of the housing, wherein the housing is configured in a shape of at least one alphanumeric character, and wherein the light-altering device includes a surface having a plurality of facets.

21. The illumination apparatus of claim 20, wherein the light-altering device alters the light by at least one of refracting, reflecting, diffracting, and dispersing.

22. An illumination apparatus, comprising:

a housing;

at least one light source for emitting light;

a light-altering device positioned relative to the housing and the light source for receiving and altering light from the light source such that the altered light illuminates at least a portion of the housing, wherein the housing is configured in a shape of at least one alphanumeric character, wherein the light source comprises a plurality of light-emitting diodes positioned along a perimeter of the housing, and wherein the light-altering device is positioned at a substantially central location relative to the housing.

23. An illumination apparatus, comprising:

a housing;

at least one light source for emitting light;

a light-altering device positioned relative to the housing and the light source for receiving and altering light from the light source such that the altered light illuminates at least a portion of the housing, wherein the housing is configured in a shape of at least one alphanumeric character, wherein the light source comprises a plurality of light-emitting diodes positioned at a substantially central location relative to the housing, and wherein the light-altering device is positioned along a perimeter of the housing.

* * * * *